(12) United States Patent
Ye

(10) Patent No.: US 9,072,811 B2
(45) Date of Patent: Jul. 7, 2015

(54) PREPARATION METHOD FOR MEDICAL POROUS TANTALUM IMPLANT MATERIAL

(71) Applicant: CHONGQING RUNZE PHARMACEUTICAL COMPANY LIMITED, Chongqing (CN)

(72) Inventor: Lei Ye, Chongqing (CN)

(73) Assignee: CHONGQING RUNZE PHARMACEUTICAL COMPANY LIMITED, Yubei, Chongqing (CN)

( * ) Notice: Subject to any disclaimer, the term of this patent is extended or adjusted under 35 U.S.C. 154(b) by 0 days.

(21) Appl. No.: 14/348,230

(22) PCT Filed: Sep. 27, 2012

(86) PCT No.: PCT/CN2012/082220
§ 371 (c)(1),
(2) Date: Mar. 28, 2014

(87) PCT Pub. No.: WO2013/044832
PCT Pub. Date: Apr. 4, 2013

(65) Prior Publication Data
US 2014/0227428 A1    Aug. 14, 2014

(30) Foreign Application Priority Data
Sep. 29, 2011 (CN) ............ 2011 1 0300340

(51) Int. Cl.
| | | |
|---|---|---|
| *A61F 2/28* | (2006.01) |
| *B23B 5/18* | (2006.01) |
| *B22F 3/10* | (2006.01) |
| *A61L 27/04* | (2006.01) |
| *B32B 5/18* | (2006.01) |
| *A61L 27/56* | (2006.01) |
| *B22F 3/11* | (2006.01) |

(52) U.S. Cl.
CPC ............. *A61L 27/047* (2013.01); *B32B 5/18* (2013.01); *A61L 27/56* (2013.01); *A61L 2400/08* (2013.01); *A61L 2430/02* (2013.01); *A61L 2430/24* (2013.01); *B22F 3/1137* (2013.01); *B22F 2999/00* (2013.01)

(58) Field of Classification Search
CPC ............ A61L 27/04; A61L 27/56; B32B 5/18
USPC ................ 427/2.26; 623/23.55; 428/613, 550
See application file for complete search history.

(56) References Cited

U.S. PATENT DOCUMENTS

| | | | | |
|---|---|---|---|---|
| 3,890,107 A | * | 6/1975 | White et al. ............ | 428/613 |
| 4,431,449 A | * | 2/1984 | Dillon et al. ............ | 75/246 |
| 7,682,704 B2 | * | 3/2010 | Dwivedi ............... | 428/547 |
| 2005/0048193 A1 | * | 3/2005 | Li et al. ................ | 427/2.24 |
| 2006/0003179 A1 | * | 1/2006 | Wang et al. ............ | 428/613 |

* cited by examiner

*Primary Examiner* — Cachet Sellman

(57) ABSTRACT

A method for preparing a porous tantalum medical implant material, which includes (a) mixing a polyethylene glycol aqueous solution and tantalum powder to form a tantalum slurry, (b) casting the tantalum slurry into an organic foam body through vibrant pressurization, and (c) performing steps of drying, degreasing, vacuum sintering and thermal treatment to obtain the porous tantalum. The solution is a 2-8 wt % polyethylene glycol aqueous solution, the frequency of vibration is 20-80 times/min, the thermal treatment is performed under $10^{-4}$-$10^{-3}$ Pa of vacuity and the temperature is first increased to 800-900° C. at a rate of 10-20° C./min and kept at 800-900° C. for 240-480 minutes, then is decreased to 400° C. at a rate of 2-5° C./min and kept at 400° C. for 120-300 minutes, and is cooled down to room temperature naturally in the furnace.

11 Claims, No Drawings

PREPARATION METHOD FOR MEDICAL POROUS TANTALUM IMPLANT MATERIAL

BACKGROUND OF THE INVENTION

1. Field of Invention

The present invention relates to a preparation method for medical porous tantalum implant material, especially to a porous tantalum used for medical implantation and a method for preparing the same.

2. Description of the Related Art

A medical porous tantalum implant material is important for specific application of treating traumatic osseous tissues, necrotic femoral tissues or the like. Such metal materials are normally porous stainless steel, porous titanium, and so on. As a porous implant material for the treatment of traumatic osseous tissues and necrotic femoral tissues, the porosity thereof should reach to 30-80%, and the pores should be all interconnected and well-distributed or partially interconnected depending on requirement. Thus, the porous implant material can make the growth phase of the osseous tissue uniform and have lower weight to fit the use of medical implantation.

Due to good biocompatibility and mechanical properties of the insoluble tantalum, the porous form thereof is potential in place of the traditional metal biomaterials mentioned above in order to be used as a medical implant material for the application of treating necrotic femoral tissues. Also, due to the harmlessness, non-toxicity, few of side effects, the rapid development of the medicine, and the further knowledge of tantalum as an implant material, the requirement of porous tantalum for medical implantation is getting more urgent than before, and the criterion of the quality of porous tantalum is getting much higher. As a porous tantalum for medical implantation, having a lot of well-distributed interconnecting pores and mechanical properties adaptable to human body are of great importance for being a novel equivalent material of bony tissues.

The medical porous metal implant material are manufactured mainly by powder sintering, like the preparation of general porous metal materials, especially by impregnating an organic foam body with metal powder and then sintering to obtain a porous metal having a foam structure with well-distributed interconnecting pores (also called "foam impregnation"). However, the porous metal materials with well-distributed interconnecting pores usually do not have sufficient mechanical properties because of the problems of the structure itself, as well as the collapse of the metal powder during sintering process. For now, such problems have not been solved according to any know research reports.

There are not many research and reports about the powder sintering process for making porous tantalum, especially few of papers has mentioned about the preparation of porous tantalum for medical implantation. CN Patent Publication No. 200510032174 discloses "Three-dimensional through-hole or part-hole interconnecting porous metal foam and its preparing method", and CN Patent Publication No. 200710152394 discloses "Porous foam tungsten and preparation method thereof". Nevertheless, the porous metal is prepared for the applications of filtering materials, or for aerospace and other applications in high temperature environments. Furthermore, the porous metal processed in such application is not porous tantalum.

Regarding porous tantalum, U.S. Pat. No. 5,282,861 discloses "Open cell tantalum structures for cancellous bone implants and cell and tissue receptors". The porous tantalum is manufactured by commercial tantalum and a supporter such as a carbon skeleton obtained from heat degradation of polyurethane precursors. The carbon skeleton has multiple dodecahedrons with mesh structures inside and wholly distributed pores, and the porosity thereof reaches to 98%. Next, the commercial tantalum is bound to the carbon skeleton to form porous metal microstructure through chemical vapor deposition (CVD) (also called "chemical deposition"). The porous tantalum material obtained by such processes has a tantalum layer having 40-60 μm of thickness, and has about 99 wt % of tantalum and about 1 wt % based on the weight of whole porous tantalum materials. The patent further discloses that the porous tantalum has 50-70 MPa of compressive strength, 2.5-3.5 GPa of elastic modulus, 63 MPa of tensile strength and 15% of the amount of plastic deformation. However, the ductility of the porous tantalum described above is obviously insufficient causing subsequent processing of the porous tantalum, such as cutting the formed material. Similarly, the porous tantalum prepared by such methods mentioned above like foam impregnation has the same problems.

SUMMARY OF THE INVENTION

The objective of the present invention is to provide a medical porous tantalum implant material with good biocompatibility and mechanical properties, and the method is easily performed and suitable for industrial manufacture.

The objective is achieved through the technical means described below:

a medical porous tantalum implant material in accordance with the present invention is produced by mixing polyethylene glycol (PEG) solution and tantalum powder to form tantalum slurry, casting the tantalum slurry into an organic foam body through vibrant pressurization, and going through steps of drying, degreasing, vacuum sintering and thermal treatment to obtain the porous tantalum. The solution is a 2-8 wt % polyethylene glycol aqueous solution, the frequency of vibration is 20-80 times/min, the thermal treatment is performed under $10^{-4}$-$10^{-3}$ Pa of vacuity and the temperature is increased to 800-900° C. at a rate of 10-20° C./min and keeping the temperature for 240-480 minutes, then decreased to 400° C. at a rate of 2-5° C./min and keeping the temperature for 120-300 minutes, and cooled down to the room temperature naturally in the furnace.

Inventors has founded that, the vibrant pressurization used in the present invention can effectively avoid the poor dispersity of the tantalum powder added the foam body, which could result problems of mechanical properties of the porous tantalum. During the development of medical porous metal materials, as an alternative support of bony tissues, the medical porous metal materials is required high porosity for good biocompatibility to let human tissues easily bind thereon. However, the higher porosity and the bigger pore diameter might weaken other mechanical properties such as strength and toughness; otherwise, the good mechanical properties could make too low porosity, bad biocompatibility and too high density. Preparation of porous tantalum numerous medical route, but the inventor creatively put forward the above steps, the process for preparing a porous tantalum implants for medical materials, especially the heat treatment process used to fully eliminate the internal stress, making the organization more porous tantalum material evenly, greatly improving the toughness of the prepared porous tantalum material, and the process is quick and easy. The obtained porous tantalum material can be tested and its impurity content less than 0.2%, its biocompatibility and bio-safety, density up 5.00-8.33 g/cm³, the porosity of up to 50 to 70%, pore diameter up to 150-500 μm; elastic modulus of up to 4.5-6.0 Gpa, extension rate of 10.0 to 11.7%, the bending strength of up to 90-110 Mpa, the compressive strength of up to 70-80 Mpa, biocompatibility, toughness is close to bone tissue in the body bearing. The characteristics of the present process are very suitable for porous tantalum bearing bone tissue substitute material for medical implants. Meanwhile, the preparation method of the process is simple, easy to control. The entire preparation process is harmless, non-polluting, non-toxic dust, having no side effects on the human body, suitable for industrial scale production. Furthermore, in the preferred preparation process can be used in a decomposed during sintering, and there is no residual organic reagents such foams will help to ensure the biocompatibility of the implant material and the biological safety.

The further characteristic of the present invention is using the tantalum powder having less than 43 μm of average diameter and less than 0.1% of oxygen content, the PEG solution as a binder and water as a dispersant to form the tantalum slurry. The organic foam body is polyurethane foam and dried by vacuum drying to remove water.

In one aspect, the solution is a 4-5 wt % PEG solution and the tantalum powder to form tantalum slurry. In one aspect, 6-9 weight parts (preferably 7 weight parts) of tantalum powder and 1 weight part of the 2-8 wt % polyvinyl alcohol solution are mixed homogeneously and agitated to form a pasty substance (i.e. tantalum slurry), the pasty substance is casted into the polyurethane foam body having 0.48-0.89 mm (preferably 0.56-0.72 mm) of pore diameter, 0.015-0.035 g/cm$^3$ (preferably 0.025 g/cm$^3$) of density and larger than 50° (preferably 50°-80°) of hardness by vibrant pressurization.

Preferably, the PEG solution uniformly is sprayed on the surface of the organic foam body, and the ratio of the weight parts of the sprayed PEG solution and the tantalum powder is 1:6.

Preferably, the tantalum powder having an average diameter of less than 43 μm and oxygen content in an amount of less than 0.1% to reduce the impurities and keep good mechanical properties; the polyurethane foam body having 0.48-0.89 mm of pore diameter, 0.015-0.035 g/cm$^3$ of density and larger than 50° of hardness is used to keep the porosity and pore diameter.

The further characteristic of the present invention is: The organic foam body with tantalum slurry is dried by vacuum drying under $10^{-2}$-1 Pa of vacuity, and the dried organic foam body with the tantalum slurry is degreased at 400-800° C. of the temperature in a protective environment of inert gas or under $10^{-4}$-$10^{-3}$ Pa of vacuity to remove PEG and the organic foam body, dried by vacuum drying under $10^{-4}$-$10^{-3}$ Pa of vacuity, and the degreased tantalum slurry is sintered by vacuum sintering under no less than $10^{-4}$-$10^{-3}$ Pa of vacuity at 2000-2200° C. and keeping the temperature for 1-5 hours to obtain the porous sintered body, and the porous sintered body is annealed.

The dried organic foam body with tantalum slurry was degreased by increasing the temperature to 400-800° C. at a rate of 0.5-5° C./min in a protective environment of argon and keeping the temperature for 30-120 minutes;

the degreased tantalum slurry is sintered to form a porous sintered body under no less than $10^{-3}$ Pa of vacuity by increasing the temperature from room temperature to 1200-1500° C. at a rate of no higher than 10-20° C./min and keeping the temperature for 1-2 hours, and then increasing the temperature to 2000-2200° C. at a rate of less than 20° C./min and keeping the temperature for at least 2-4 hours to obtain the porous sintered body;

the porous sintered body is cooled down under no less than $10^{-3}$ Pa of vacuity by decreasing to 800° C. the temperature at a rate of between 10-25° C./min by stages of which is 30-90 minutes per stage and then decreased to room temperature naturally;

the porous sintered body is annealed under $10^{-4}$-$10^{-3}$ Pa of vacuity by increasing the temperature to 800-900° C. at a rate of 15° C./min and keeping the temperature for 260-320 minutes, and then decreasing the temperature to 400° C. at a rate of 3° C./min and keeping the temperature for 120-300 minutes, and then to room temperature at a rate of 18-23° C./min.

Based on the means described above, the further characteristic of the present invention is: the organic foam body with tantalum slurry was dried under $10^{-2}$-1 Pa of vacuity at 60-100° C. of the temperature for 4-8 hours; the dried organic foam body with the tantalum slurry was degreased by increasing the temperature to 600-800° C. by stages in a protective environment of argon (99.9999% of purity), wherein the dried organic foam body with the tantalum slurry was degreased by increasing the temperature from room temperature to 400° C. at a rate of 1-5° C./min and keeping the temperature for 30-60 minutes, and then increasing the temperature from 400° C. to 600-800° C. at a rate of 0.5-1.5° C./min and keeping the temperature for 60-120 minutes; the degreased organic foam body with the tantalum slurry was sintered to form a porous sintered body by increasing the temperature to a range of 1200-1250° C. at a rate of 10-15° C./min and keeping the temperature for 30-60 minutes under $10^{-4}$-$10^{-3}$ Pa of vacuity, then increasing the temperature to 1500° C. at a rate of 10-20° C./min and keeping the temperature for 30-60 minutes under $10^{-4}$-$10^{-3}$ Pa of vacuity, and then increasing the temperature to a range of 2000-2200° C. at a rate of 6-20° C./min and keeping the temperature for 120-240 minutes under $10^{-4}$-$10^{-3}$ Pa of vacuity; the porous sintered body is cooled down under $10^{-4}$-$10^{-3}$ Pa of vacuity by decreasing the temperature to 1500-1600° C. at a rate of 10-20° C./min and keeping the temperature for 30-60 minute, then decreasing the temperature to 1200-1250° C. at a rate of 12-20° C./min and keeping the temperature for 60-90 minutes, and then decreasing the temperature to 800° C. at a rate of 10-20° C./min, and the porous sintered body is cooled down naturally; the porous sintered body is annealed by increasing the temperature to 800-900° C. at a rate of 15-30° C./min and keeping the temperature for 260-320 minute under $10^{-4}$-$10^{-3}$ Pa of vacuity, and then decreasing the temperature to 400° C. at a rate of 3° C./min and keeping the temperature for 120-300 minute, and then to room temperature at a rate of 18-23° C./min.

Vacuum drying and degreasing is attributed to reducing the impurities in the porous tantalum, improving biocompatibility bio-safety and mechanical properties. The optimization of the organic foam body overcomes the difficulty of collapse of the foam skeleton during sintering. The optimization of the conditions of the sintering and annealing processes is favorable to bettering the mechanical properties of the porous tantalum such as ductility.

DETAILED DESCRIPTION OF THE INVENTION

The present invention is more specifically described in the following paragraphs by reference to the drawings attached only by way of examples. It should be noted that the embodiments are not limitation of the scope of the present invention.

Example 1

12.2 g of polyethylene glycol (PEG) was put in a container filled in 240 ml of water, and then the container was put on a hotplate. PEG and water are heated and agitated to form a PEG solution. 60 g of tantalum powder with less than 43 μm of diameter and less than 0.1% of oxygen content was scaled by a 200 g balance and added to 50 ml of the PEG solution (the PEG solution was cooled). The tantalum powder and the PEG solution were mixed and agitated homogeneously to form tantalum slurry. The tantalum slurry was casted into a 10×10×30 mm porous polyurethane foam body (0.48 mm of average pore diameter, 0.025 g/cm$^3$ of density and 50° of hardness) by vibrant pressurization. Then, the polyurethane foam body filled with the tantalum slurry was put into a porcelain dish placed in a vacuum drier. The polyurethane foam body filled with the tantalum slurry was dried in the vacuum drier at 60° C. for 8 hours under 1 Pa of vacuity. The dried polyurethane foam body filled with the tantalum slurry was degreased at 600° C. for 120 minutes under lower than $10^{-4}$ Pa of vacuity. The dried polyurethane foam and the dried tantalum slurry were separated after the process of degreasing. Then, the dried tantalum slurry are sintered in a vacuum sintering furnace at 2000° C. for 2 hours under $10^{-4}$ Pa of vacuity to form a porous sintered body. The argon is employed as a protective gas during sintering. The porous sintered body was cleaned out of the dust and dirt and then treated with normal post-treatments to obtain a porous tantalum.

The density, porosity, pore diameter and other mechanical properties of the obtained porous tantalum were tested by standard test methods such as GB/T5163-2006, GB/T5249-1985, GB/T6886-2001 and the like. The porous tantalum has three-dimensional interconnecting pores and less than 0.5% of impurities. The interconnecting pores are well-distributed. The tested porous tantalum has 6.7 g/cm3 of density, higher than 66% of porosity, 405 μm of average pore diameter, 4.8 GPa of elastic modulus, 95 MPa of yield strength, 72 MPa of compressive strength and 10.8% of percentage elongation.

Example 2

10 g of polyvinyl alcohol was put in a container filled in 200 ml of water, and then the container was put on a hotplate. The polyvinyl alcohol and water are heated and agitated to form a polyvinyl alcohol solution. 40 g of tantalum powder with less than 43 μm of diameter and less than 0.1% of oxygen content was scaled by a 200 g balance an added to 32 ml of the polyvinyl alcohol solution (the polyvinyl alcohol solution was cooled). The tantalum powder and the PEG solution were mixed and agitated homogeneously to form tantalum slurry. The tantalum slurry was casted into a 10×10×25 mm porous polyurethane foam body (0.56 mm of average pore diameter, 0.030 g/cm$^3$ of density and 60° of hardness) by vibrant pressurization. Then, the polyurethane foam body filled with the tantalum slurry was put into a porcelain dish placed in a vacuum drier. The polyurethane foam body filled with the tantalum slurry was dried in the vacuum drier at 100° C. for 4 hours under $10^{-2}$ Pa of vacuity. The dried polyurethane foam body filled with the tantalum slurry was degreased at 800° C. for 120 minutes under $10^{-4}$ Pa of vacuity. The dried polyurethane foam body and the dried tantalum slurry were separated after the process of degreasing. Then, the dried tantalum slurry are sintered in a vacuum sintering furnace at 2100° C. for 4 hours under $10^{-4}$ Pa of vacuity and formed in a porous sintered body. The argon is employed as a protective gas during sintering. The porous sintered body was cleaned out of the dust and dirt and then treated with thermal treatment to obtain a porous tantalum. The thermal treatment is performed under $10^{-4}$ Pa of vacuity. The temperature is increased to 800-900° C. at a rate of 15° C./min, and kept for 320 min, then decreased to 400° C. at a rate of 3° C./min and kept for 300 min, and then decreased to room temperature at a rate of 3° C./min at a rate of 19° C./min to obtain the porous tantalum.

The density, porosity, pore diameter and other mechanical properties of the obtained porous tantalum were tested by standard test methods such as GB/T5163-2006, GB/T5249-1985, GB/T6886-2001 and the like. The porous tantalum has three-dimensional interconnecting pores and less than 0.5% of impurities. The interconnecting pores are well-distributed. The tested porous tantalum has 5.05 g/cm$^3$ of density, 58% of porosity, 330 μm of average pore diameter, 6.0 GPa of elastic modulus, 93 MPa of yield strength, 74 MPa of compressive strength and 11.5% of percentage elongation.

Example 3

11 g of PEG was put in a container filled in 220 ml of water, and then the container was put on the hotplate. The PEG and water are heated and agitated to form a PEG solution. 45 g of tantalum powder with less than 43 μm of diameter and less than 0.1% of oxygen content was scaled by a 200 g balance an added to 36 ml of the PEG solution (the PEG solution was cooled). The tantalum powder and the PEG solution were mix and agitated homogeneously to form tantalum slurry. The tantalum slurry was casted into a 8×8×25 mm porous polyurethane foam body (0.70 mm of average pore diameter, 0.035 g/cm$^3$ of density and 70° of hardness) by vibrant pressurization. Then, the polyurethane foam body filled with the tantalum slurry was put into a porcelain dish placed in a vacuum drier. The polyurethane foam body filled with the tantalum slurry was dried in the vacuum drier at 80° C. for 6 hours under $10^{-1}$ Pa of vacuity. The dried polyurethane foam filled with the tantalum slurry was degreased at 700° C. for 90 minutes under $10^{-3}$ Pa of vacuity. The dried polyurethane foam body and the dried tantalum slurry were separated after the process of degreasing. Then, the dried tantalum slurry are sintered in a vacuum sintering furnace at 2200° C. for 2.5 hours under $10^{-3}$ Pa of vacuity and formed in a porous sintered body. The argon is employed as a protective gas during sintering. The porous sintered body was cleaned out of the dust and dirt and then treated with thermal treatment. The thermal treatment is performed under $10^{-3}$ Pa of vacuity. The temperature is increased to 800-900° C. at a rate of 17° C./min, and kept for 250 min, then decreased to 400° C. at a rate of 6° C./min and kept for 122 min, and then decreased to room temperature at a rate of 18° C./min to obtain the porous tantalum.

The density, porosity, pore diameter and other mechanical properties of the obtained porous tantalum were tested by standard test methods such as GB/T5163-2006, GB/T5249-1985, GB/T6886-2001 and the like. The porous tantalum has three-dimensional interconnecting pores and less than 0.5% of impurities. The interconnecting pores are well-distributed. The tested porous tantalum has 7.5 g/cm$^3$ of density, 55% of porosity, 130 μm of average pore diameter, 5.2 GPa of elastic modulus, 106 MPa of yield strength, 72 MPa of compressive strength and 10.4% of percentage elongation.

Example 4

12 g of PEG was put in a container filled in 230 ml of water, and then the container was put on a hotplate. The PEG and water are heated and agitated to form a PEG solution. 50 g of tantalum powder with less than 43 μm of diameter and less than 0.1% of oxygen content was scaled by a 200 g balance an added to 40 ml of the PEG solution. The tantalum powder and the polyvinyl alcohol solution were mixed and agitated homogeneously to form tantalum slurry. The tantalum slurry was casted into a 12×12×30 mm porous polyurethane foam body (0.60 mm of average pore diameter, 0.027 g/cm³ of density and 80° of hardness) until the pores of the polyurethane foam body were filled with the tantalum slurry. Then, the polyurethane foam body filled with the tantalum slurry was put into a porcelain dish placed in a vacuum drier. The polyurethane foam body filled with the tantalum slurry was dried in the vacuum drier at 90° C. for 5 hours under 1 Pa of vacuity. The dried polyurethane foam body filled with the tantalum slurry was degreased at 500° C. for 120 minutes under $10^{-4}$-$10^{-3}$ Pa of vacuity. The dried polyurethane foam body and the dried tantalum slurry were separated after the process of degreasing. Then, the dried tantalum slurry are sintered in a vacuum sintering furnace at 2150° C. for 2 hours under $10^{-4}$ Pa of vacuity and formed in a porous sintered body. The argon is employed as a protective gas during sintering. The porous sintered body was cleaned out of the dust and dirt and then treated by normal post-treatments to obtain a porous tantalum.

The density, porosity, pore diameter and other mechanical properties of the obtained porous tantalum were tested by standard test methods such as GB/T5163-2006, GB/T5249-1985, GB/T6886-2001 and the like. The porous tantalum has three-dimensional interconnecting pores and less than 0.5% of impurities. The interconnecting pores are well-distributed. The tested porous tantalum has 8.33 g/cm³ of density, 60% of porosity, 200 μm of average pore diameter, 5.0 GPa of elastic modulus, 99 MPa of yield strength, 72 MPa of compressive strength and 11% of percentage elongation.

Example 5

Tantalum powder having less than 43 μm of diameter and less than 0.1% of the oxygen content as a raw material was mixed with a PEG solution as a binder solution to form tantalum slurry. The tantalum slurry was casted into a polyurethane foam body. The polyurethane foam body with the tantalum slurry was dried, degreased, vacuum sintered, vacuum annealed and treated with normal post-treatments to obtain a porous tantalum.

In the exemplary embodiment, the poly urethane foam body has 0.56-0.72 mm of pore diameter, 0.025 g/cm³ of density and 50°-80° of hardness. The polyurethane foam body with the tantalum slurry was dried under $10^{-2}$-1 Pa of vacuity to remove water. The dried polyurethane foam body and PEG are separated from the dried tantalum slurry at 400-800° C. of the temperature under $10^{-4}$-$10^{-3}$ Pa of vacuity or in a protective environment of inert gas with keeping the temperature for 30-120 minutes. The dried tantalum slurry was sintered at 2000-2200° C. under $10^{-4}$-$10^{-3}$ Pa of vacuity and keeping the temperature for 1-5 hours. The argon or other alternative inert gas was employed as a protective gas when keeping the temperature during sintering process, to obtain a porous sintered body. After sintered, the porous sintered body was annealed by keeping the temperature at 1000-1250° C. for 1-4 hours under $10^{-4}$-$10^{-3}$ Pa of vacuity, and then treated with normal post-treatments to obtain a porous tantalum.

The density, porosity, pore diameter and other mechanical properties of the obtained porous tantalum were tested by standard test methods such as GB/T5163-2006, GB/T5249-1985, GB/T6886-2001 and the like. The porous tantalum has three-dimensional interconnecting pores and less than 0.5% of impurities. The interconnecting pores are well-distributed. The tested porous tantalum has 6.3 g/cm³ of density, 65% of porosity, 290 μm of average pore diameter, 4.9 GPa of elastic modulus, 92 MPa of yield strength, 79 MPa of compressive strength and 11.6% of percentage elongation.

Besides the processes mentioned above in Example 5, people skilled in the art can make changes and modifications of the conditions to obtain the porous tantalum of the present invention.

TABLE 1

| Example | Diameter of tantalum powder (mm)/ Oxygen content (%) | Weight concentration of PEG solution | Tantalum powder (weight part)/ PEG solution (weight part) | Weight ratio of tantalum powder and sprayed PEG solution on the polyurethane foam body | Pore diameter of polyurethane foam body (mm) | Density of polyurethane foam body (g/cm3) |
|---|---|---|---|---|---|---|
| 6 | <38/0.1% | 2.8% | 6:1 | 6:1 | 0.80 | 0.025 |
| 7 | <40/0.1% | 8% | 7.5:1 | 5.5:1 | 0.68 | 0.035 |
| 8 | <43/0.1% | 6% | 7:1 | 4:1 | 0.70 | 0.030 |
| 9 | <39/0.1% | 3.4% | 8.8:1 | 7:1 | 0.50 | 0.027 |

TABLE 2

| Example | Vacuity of drying (Pa)/ Temperature (° C.)/Time (h) | Atmosphere of degreasing (Pa)/Temperature (° C.)/ Time (min) | Atmosphere of sintering (Pa)/ Temperature (° C.)/ Time (min) | The atmosphere of annealing (Pa)/ The rate of increasing or decreasing the temperature (° C./min)/ Temperature (° C.)/ Time of keeping temperature (min) |
|---|---|---|---|---|
| 6 | 1/75/5.5 | increasing from room temperature to at a rate of 1° C./min and keeping the temperature for 60 min; increasing from 400° C. to | 6° C./min and keeping the temperature for 240 min under $10^{-3}$ Pa of vacuity; | $10^{-4}$ Pa/ increasing to 1030° C. at a rate of 15° C./min and keeping the |

TABLE 2-continued

| Example | Vacuity of drying (Pa)/ Temperature (° C.)/Time (h) | Atmosphere of degreasing (Pa)/Temperature (° C.)/ Time (min) | Atmosphere of sintering (Pa)/ Temperature (° C.)/ Time (min) | The atmosphere of annealing (Pa)/ The rate of increasing or decreasing the temperature (° C./min)/ Temperature (° C.)/ Time of keeping temperature (min) |
|---|---|---|---|---|
|  |  | 600° C. at a rate of 0.5° C./min and keeping the temperature for 120 min. | increasing from room temperature to 1200° C. at a rate of 10° C./min and keeping the temperature for 60 min under $10^{-4}$ Pa of vacuity; decreasing to 1520° C. at a rate of 11° C./min and keeping the temperature for 60 min under $10^{-4}$-$10^{-3}$ Pa of vacuity; decreasing to 1200° C. at a rate of 13° C./min and keeping the temperature for 90 min; decreasing to 800° C. at a rate of 13° C./min, and natural cooling. | temperature for 480 min/ decreasing to 1000° C. at a rate of 5° C./min and keeping the temperature for 180 min;/ decreasing to 800° C. at a rate of 11° C./min and keeping the temperature for 108 min;/ decreasing to room temperature at a rate of 21° C./min |
| 7 | 1/65/6.5 | increasing from room temperature to 400° C. at a rate of 1.5° C./min and keeping the temperature for 58 min; increasing from 400° C. to 650° C. at a rate of 0.6° C./min and keeping the temperature for 110 min | increasing to 1210° C. at a rate of 11° C./min and keeping the temperature for 58 min under $10^{-4}$ Pa of vacuity; increasing to 1270° C. at a rate of 12° C./min and keeping the temperature for 55 min; increasing to 2050° C. at a rate of 8° C./min and keeping the temperature for 220 min under $10^{-3}$ Pa of vacuity; decreasing to 1530° C. at a rate of 12° C./min and keeping the temperature for 55 min under $10^{-4}$-$10^{-3}$ Pa of vacuity; decreasing to 1210° C. at a rate of 14° C./min and keeping the temperature for 85 min; decreasing to 800° C. at a rate of 14° C./min and natural cooling | $10^{-4}$ Pa/ increasing to 1050° C. at a rate of 17° C./min and keeping the temperature for 450 min/ decreasing to 1000° C. at a rate of 6° C./min and keeping the temperature for 150 min;/ decreasing to 800° C. at a rate of 12° C./min and keeping the temperature for 102 min;/ decreasing to room temperature at a rate of 22° C./min |
| 8 | 1/45/7.5 | increasing from room temperature to 400° C. at a rate of 2° C./min and keeping the temperature for 56 min; increasing from 400° C. to 680° C. at a rate of 0.7° C./min and keeping the temperature for 100 min; | increasing to 1220° C. at a rate of 12° C./min and keeping the temperature for 55 min under $10^{-4}$ Pa of vacuity; increasing to 1300° C. at a rate of 13° C./min and keeping the | $10^{-4}$ Pa/ increasing to 1100° C. at a rate of 20° C./min and keeping the temperature for 420 min/ decreasing to 1000° C. at a rate of |

TABLE 2-continued

| Example | Vacuity of drying (Pa)/ Temperature (° C.)/Time (h) | Atmosphere of degreasing (Pa)/Temperature (° C.)/ Time (min) | Atmosphere of sintering (Pa)/ Temperature (° C.)/ Time (min) | The atmosphere of annealing (Pa)/ The rate of increasing or decreasing the temperature (° C./min)/ Temperature (° C.)/ Time of keeping temperature (min) |
|---|---|---|---|---|
| | | | temperature for 50 min; increasing to 2100° C. at a rate of 10° C./min and keeping the temperature for 200 min under $10^{-3}$ Pa of vacuity; decreasing to 1540° C. at a rate of 13° C./min and keeping the temperature for 50 min under $10^{-4}$-$10^{-3}$ Pa of vacuity; decreasing to 1220° C. at a rate of 15° C./min and keeping the temperature for 80 min; decreasing to 800° C. at a rate of 15° C./min and natural cooling. | 7° C./min and keeping the temperature for 130 min;/ decreasing to 800° C. at a rate of 13° C./min and keeping the temperature for 96 min;/ decreasing to room temperature at a rate of 23° C./min |
| 9 | 1/55/7 | increasing from room temperature to 400° C. at a rate of 2.5° C./min and keeping the temperature for 55 min; increasing from 400° C. to 700° C. at a rate of 0.8° C./min and keeping the temperature for 90 min; | increasing to 1220° C. at a rate of 12° C./min and keeping the temperature for 55 min under $10^{-4}$ Pa of vacuity; increasing to 1300 C. at a rate of 13° C./min and keeping the temperature for 50 min; increasing to 2100° C. at a rate of 10° C./min and keeping the temperature for 200 min under $10^{-3}$ Pa of vacuity; decreasing to 1540° C. at a rate of 13° C./min and keeping the temperature for 50 min under $10^{-4}$-$10^{-3}$ Pa of vacuity; decreasing to 1220° C. at a rate of 15° C./min and keeping the temperature for 80 min; decreasing to 800° C. at a rate of 15° C./min and natural cooling. | $10^{-4}$ Pa/ increasing to 1150° C. at a rate of 22° C./min and keeping the temperature for 360 min/ decreasing to 1000° C. at a rate of 8° C./min and keeping the temperature for 120 min;/ decreasing to 800° C. at a rate of 14° C./min and keeping the temperature for 90 min;/ decreasing to room temperature at a rate of 24° C./min |

TABLE 3

The mechanical properties of the porous tantalum prepared in Example 7-13

| Example | 6 | 7 | 8 | 9 |
|---|---|---|---|---|
| Density (g/cm3) | 6.4 | 7.3 | 8.0 | 5.8 |
| Porosity (%) | 52 | 70 | 64 | 59 |
| Pore diameter (μm) | 150 | 456 | 389 | 290 |
| Elastic modulus (GPa) | 4.6 | 6.0 | 5.4 | 5.0 |
| Yield strength (MPa) | 110 | 100 | 90 | 80 |
| Compressive strength (MPa) | 80 | 76 | 70 | 73 |
| Percentage elongation (%) | 10.0 | 11.5 | 10.6 | 11.0 |
| Example | 6 | 7 | 8 | 9 |
| Density (g/cm3) | 6.4 | 7.3 | 8.0 | 5.8 |
| Porosity (%) | 52 | 70 | 64 | 59 |
| Pore diameter (μm) | 150 | 456 | 389 | 290 |
| Elastic modulus (GPa) | 4.6 | 6.0 | 5.4 | 5.0 |

What is claimed is:

1. A method for preparing a porous tantalum medical implant material, comprising:
   (a) mixing a polyethylene glycol (PEG) solution and tantalum powder to form a tantalum slurry wherein the solution is a 2-8 wt % polyethylene glycol aqueous solution;
   (b) casting the tantalum slurry into an organic foam body through vibrant pressurization wherein the vibrant pressurization is performed using a frequency of vibration of 20-80 times/min;
   (c) performing steps of drying, degreasing, vacuum sintering and thermal treatment to thereby obtain the porous tantalum, wherein the thermal treatment is performed under $10^{-4}$-$10^{-3}$ Pa of vacuity and the temperature is increased to 800-900° C. at a rate of 10-20° C./min and maintaining the temperature at 800-900° C. for 240-480 minutes, then decreasing the temperature to 400° C. at a rate of 2-5° C./min and maintaining the temperature at 400° C. for 120-300 minutes, and cooling the temperature down to room temperature naturally in the furnace.

2. The method as claimed in claimed 1, wherein the tantalum powder has an average diameter of less than 43 μm and oxygen content in an amount of less than 0.1%, and the material has 40-80% of porosity and 150-500 μm of pore diameter; the organic foam body is a polyurethane foam body having 0.48-0.89 mm of pore diameter, 0.015-0.035 g/cm³ of density and larger than 50° of hardness.

3. The method as claimed in claimed 1 or 2, wherein 6-9 weight parts of tantalum powder and 1 weight part of the 2-8 wt % polyethylene glycol aqueous solution are mixed homogeneously and agitated to form the tantalum slurry.

4. The method as claimed in claimed 3, wherein the vibrant pressurization is performed using a frequency of vibration is 60 times/min, and a pressure is 0.1 MPa; the organic foam body has 0.56-0.72 mm of pore diameter, 0.025 g/cm³ of density and 50°-80° of hardness, and the tantalum slurry is made by mixing 7 weight parts of tantalum powder of the tantalum powder and 1 weight part of the PEG solution.

5. The method as claimed in claimed 1 or 2, wherein the tantalum slurry is filled into the organic foam body through vibrant pressurization, the PEG solution is sprayed uniformly on the surface of the organic foam body, and the ratio of the weight parts of the sprayed PEG solution and the tantalum powder is 1:6.

6. The method as claimed in claim 3, wherein the tantalum slurry is filled into the organic foam body through vibrant pressurization, the PEG solution is sprayed uniformly on the surface of the organic foam body, and the ratio of the weight parts of the sprayed PEG solution and the tantalum powder is 1:6.

7. The method as claimed in claim 4, wherein the tantalum slurry is filled into the organic foam body through vibrant pressurization, the PEG solution is sprayed uniformly on the surface of the organic foam body, and the ratio of the weight parts of the sprayed PEG solution and the tantalum powder is 1:6.

8. The method as claimed in claim 1 or 2, wherein the organic foam body with tantalum slurry is dried by vacuum drying under $10^{-2}$-1 Pa of vacuity, and the dried organic foam body with the tantalum slurry is degreased at 400-800° C. of the temperature in a protective environment of inert gas or under $10^{-4}$-$10^{-3}$ Pa of vacuity to remove PEG and the organic foam body, dried by vacuum drying under $10^{-4}$-$10^{-3}$ Pa of vacuity, and the degreased tantalum slurry is sintered by vacuum sintering under no less than $10^{-4}$-$10^{-3}$ Pa of vacuity at 2000-2200° C. and keeping the temperature for 1-5 hours to obtain the porous sintered body, and the porous sintered body is annealed;
   the dried organic foam body with tantalum slurry was degreased by increasing the temperature to 400-800° C. at a rate of 0.5-5° C./min in a protective environment of argon and keeping the temperature for 30-120 minutes;
   the degreased tantalum slurry is sintered to form a porous sintered body under no less than $10^{-3}$ Pa of vacuity by increasing the temperature from room temperature to 1200-1500° C. at a rate of no higher than 10-20° C./min and keeping the temperature for 1-2 hours, and then increasing the temperature to 2000-2200° C. at a rate of less than 20° C./min and keeping the temperature for at least 2-4 hours to obtain the porous sintered body;
   the porous sintered body is cooled down under no less than $10^{-3}$ Pa of vacuity by decreasing to 800° C. the temperature at a rate of between 10-25° C./min by stages of which is 30-90 minutes per stage and then decreased to room temperature naturally; and
   the porous sintered body is annealed under $10^{-4}$-$10^{-3}$ Pa of vacuity by increasing the temperature to 800-900° C. at a rate of 15° C./min and keeping the temperature for 260-320 minutes, and then decreasing the temperature to 400° C. at a rate of 3° C./min and keeping the temperature for 120-300 minutes, and then to room temperature at a rate of 18-23° C./min.

9. The method as claimed in claim 7, wherein the dried organic foam body with tantalum slurry was degreased by increasing the temperature to 400-800° C. at a rate of 0.5-5° C./min in a protective environment of argon and keeping the temperature for 30-120 minutes;
   the degreased tantalum slurry is sintered to form a porous sintered body under no less than $10^{-3}$ Pa of vacuity by increasing the temperature from room temperature to 1200-1500° C. at a rate of no higher than 10-20° C./min and keeping the temperature for 1-2 hours, and then increasing the temperature to 2000-2200° C. at a rate of less than 20° C./min and keeping the temperature for at least 2-4 hours to obtain the porous sintered body;
   the porous sintered body is cooled down under no less than $10^{-3}$ Pa of vacuity by decreasing to 800° C. the temperature at a rate of between 10-25° C./min by stages of which is 30-90 minutes per stage and then decreased to room temperature naturally; and
   the porous sintered body is annealed under $10^{-4}$-$10^{-3}$ Pa of vacuity by increasing the temperature to 800-900° C. at a rate of 15° C./min and keeping the temperature for 260-320 minutes, and then decreasing the temperature to 400° C. at a rate of 3° C./min and keeping the temperature for 120-300 minutes, and then to room temperature at a rate of 18-23° C./min.

10. The method as claimed in claim 1 or 2, wherein the organic foam body with tantalum slurry was dried under $10^{-2}$-1 Pa of vacuity at 60-100° C. of the temperature for 4-8 hours; the dried organic foam body with the tantalum slurry was degreased by increasing the temperature to 600-800° C. by stages in a protective environment of argon (99.9999% of purity), wherein the dried organic foam body with the tantalum slurry was degreased by increasing the temperature from room temperature to 400° C. at a rate of 1-5° C./min and keeping the temperature for 30-60 minutes, and then increasing the temperature from 400° C. to 600-800° C. at a rate of 0.5-1.5° C./min and keeping the temperature for 60-120 minutes; the degreased organic foam body with the tantalum slurry was sintered to form a porous sintered body by increasing the temperature to a range of 1200-1250° C. at a rate of 10-15° C./min and keeping the temperature for 30-60 minutes under $10^{-4}$-$10^{-3}$ Pa of vacuity, then increasing the temperature to 1500° C. at a rate of 10-20° C./min and keeping the temperature for 30-60 minutes under $10^{-4}$-$10^{-3}$ Pa of vacuity, and then increasing the temperature to a range of 2000-2200° C. at a rate of 6-20° C./min and keeping the temperature for 120-240 minutes under $10^{-4}$-$10^{-3}$ Pa of vacuity; the porous sintered body is cooled down under $10^{-4}$-$10^{-3}$ Pa of vacuity by decreasing the temperature to 1500-1600° C. at a rate of 10-20° C./min and keeping the temperature for 30-60 minute, then decreasing the temperature to 1200-1250° C. at a rate of 12-20° C./min and keeping the temperature for 60-90 minutes, and then decreasing the temperature to 800° C. at a rate of 10-20° C./min, and the porous sintered body is cooled down naturally; the porous sintered body is annealed by increasing the temperature to 800-900° C. at a rate of 15-30° C./min and keeping the temperature for 260-320 minute under $10^{-4}$-$10^{-3}$ Pa of vacuity, and then decreasing the temperature to 400° C. at a rate of 3° C./min and keeping the temperature for 120-300 minute, and then to room temperature at a rate of 18-23° C./min.

11. The method as claimed in claim 7, wherein the organic foam body with tantalum slurry was dried under $10^{-2}$-1 Pa of vacuity at 60-100° C. of the temperature for 4-8 hours;

the dried organic foam body with the tantalum slurry was degreased by increasing the temperature to 600-800° C. by stages in a protective environment of argon (99.9999% of purity), wherein the dried organic foam body with the tantalum slurry was degreased by increasing the temperature from room temperature to 400° C. at a rate of 1-5° C./min and keeping the temperature for 30-60 minutes, and then increasing the temperature from 400° C. to 600-800° C. at a rate of 0.5-1.5° C./min and keeping the temperature for 60-120 minutes;

the degreased organic foam body with the tantalum slurry was sintered to form a porous sintered body by increasing the temperature to a range of 1200-1250° C. at a rate of 10-15° C./min and keeping the temperature for 30-60 minutes under $10^{-4}$-$10^{-3}$ Pa of vacuity, then increasing the temperature to 1500° C. at a rate of 10-20° C./min and keeping the temperature for 30-60 minutes under $10^{-4}$-$10^{-3}$ Pa of vacuity, and then increasing the temperature to a range of 2000-2200° C. at a rate of 6-20° C./min and keeping the temperature for 120-240 minutes under $10^{-4}$-$10^{-3}$ Pa of vacuity;

the porous sintered body is cooled down under $10^{-4}$-$10^{-3}$ Pa of vacuity by decreasing the temperature to 1500-1600° C. at a rate of 10-20° C./min and keeping the temperature for 30-60 minute, then decreasing the temperature to 1200-1250° C. at a rate of 12-20° C./min and keeping the temperature for 60-90 minutes, and then decreasing the temperature to 800° C. at a rate of 10-20° C./min, and the porous sintered body is cooled down naturally; and the porous sintered body is annealed by increasing the temperature to 800-900° C. at a rate of 15-30° C./min and keeping the temperature for 260-320 minute under $10^{-4}$-$10^{-3}$ Pa of vacuity, and then decreasing the temperature to 400° C. at a rate of 3° C./min and keeping the temperature for 120-300 minute, and then to room temperature at a rate of 18-23° C./min.

* * * * *